United States Patent
Matz et al.

(10) Patent No.: US 9,629,537 B2
(45) Date of Patent: Apr. 25, 2017

(54) SYSTEM FOR EYE EXAMINATION BY MEANS OF STRESS-DEPENDENT PARAMETERS

(71) Applicants: Carl Zeiss Meditec AG, Jena (DE); Carl Zeiss AG, Oberkochen (DE)

(72) Inventors: Holger Matz, Unterschneidheim (DE); Stefan Saur, Aalen (DE); Carolin Schiele, Aufhausen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 14/966,728

(22) Filed: Dec. 11, 2015

(65) Prior Publication Data
US 2016/0192835 A1    Jul. 7, 2016

(30) Foreign Application Priority Data
Dec. 12, 2014 (DE) .......... 10 2014 018 516

(51) Int. Cl.
| | |
|---|---|
| *A61B 3/14* | (2006.01) |
| *A61B 3/00* | (2006.01) |
| *A61B 3/13* | (2006.01) |
| *A61B 90/00* | (2016.01) |
| *A61B 3/10* | (2006.01) |
| *A61B 3/12* | (2006.01) |

(52) U.S. Cl.
CPC .......... *A61B 3/0025* (2013.01); *A61B 3/0058* (2013.01); *A61B 3/102* (2013.01); *A61B 3/1225* (2013.01); *A61B 3/13* (2013.01); *A61B 3/132* (2013.01); *A61B 90/00* (2016.02)

(58) Field of Classification Search
USPC ................................. 351/200–246
See application file for complete search history.

(56) References Cited

U.S. PATENT DOCUMENTS

| | | | |
|---|---|---|---|
| 2009/0040602 A1* | 2/2009 | Spilman | G03F 7/70566 359/386 |
| 2012/0019777 A1 | 1/2012 | Hauger et al. | |
| 2014/0362343 A1 | 12/2014 | Hauger et al. | |

(Continued)

FOREIGN PATENT DOCUMENTS

DE    10 2013 009 817 A1    12/2014

OTHER PUBLICATIONS

B.F. Kennedy et al., "Strain estimation in phase-sensitive optical coherence elastography", Biomedical Optics Express, vol. 3, No. 8, Jul. 17, 2012, pp. 1865-1879.

(Continued)

*Primary Examiner* — Mohammed Hasan
(74) *Attorney, Agent, or Firm* — Nixon Peabody LLP; Jeffrey L. Costellia

(57) ABSTRACT

The present disclosure relates to a system for examining an eye. The system comprises a microscopy system for generating an image plane image of an object region. An OCT system of the system is configured to acquire OCT data from the object region which reproduce the object region in different stress states. A data processing unit of the system is configured to determine at least one value of a stress-dependent parameter, depending on the OCT data. The system generates an output image that is dependent on the image plane image and is furthermore dependent on the stress-dependent parameter.

17 Claims, 7 Drawing Sheets

(56) References Cited

U.S. PATENT DOCUMENTS

| | | | |
|---|---|---|---|
| 2015/0119835 A1* | 4/2015 | Seiwert | A61B 3/102 |
| | | | 604/319 |
| 2016/0081545 A1* | 3/2016 | Hauger | G02B 21/025 |
| | | | 351/221 |
| 2016/0089015 A1* | 3/2016 | Eslami | A61B 5/7217 |
| | | | 351/206 |

OTHER PUBLICATIONS

J. Greenleaf et al., "Selected Methods for Imaging Elastic Properties of Biological Tissues", Annual Review of Biomedical Engineering, vol. 5, 2003, pp. 57-78.
B.F. Kennedy et al., "In vivo three-dimensional optical coherence elastography", Optics Express, vol. 19, No. 7, Mar. 23, 2011, pp. 6623-6634.
M. Razani et al., "Optical Coherence Tomography detection of shear wave propagation in layered tissue equivalent phantoms", Proc. of SPIE, vol. 8565, 2013, pp. 1-7, Mar.
R.K. Manapuram et al., "In vivo estimation of elastic wave parameters using phase-stabilized swept source optical coherence elastography", Journal of Biomedical Optics, vol. 17, No. 10, Oct. 2012, pp. 1-3.
S. Binder et al., "Feasibility of Intrasurgical Spectral-Domain Optical Coherence Tomography", Retina, vol. 31, No. 7, 2011, pp. 1332-1336.
Y. Zhao et al., "Integrated multimodal optical microscopy for structural and functional imaging of engineered and natural skin", Journal of Biophotonics, Feb. 28, 2012, pp. 1-12.
German Office Action, with translation thereof, for corresponding DE application No. 10 2014 018 516.8 dated Sep. 7, 2015.

\* cited by examiner

SYSTEM FOR EYE EXAMINATION BY MEANS OF STRESS-DEPENDENT PARAMETERS

PRIOR ART

Macular pucker (also referred to as epiretinal gliosis) is a disease of the eye in which the posterior vitreous humour changes, a transparent, cellophanelike membrane forming on the central retina (macula). The membrane is transparent or semitransparent and typically has a thickness of a few micrometers. The membrane slowly shrinks and warps and consequently deforms the retina. As a result, wrinkles form in the retina (the English word "pucker" means "wrinkle"). This can have the effect that for the patient the central visual field is reduced and visual perception is distorted (metamorphopsia). The mechanical forces which are exerted on the tissue of the retina lead to an accumulation of water, which causes a swelling of the retina (macular oedema). This additionally reduces the central visual field. If the patient's sight is restricted too much, epiretinal gliosis has to be treated by an intervention.

In said intervention, firstly the posterior vitreous humour is removed (vitrectomy). Afterwards, the epiretinal membrane is pulled away from the retina with the aid of fine forceps, the membrane being plucked from the retina at a shallow angle by means of the forceps. If appropriate, the surgeon additionally removes the inner limiting membrane (membrana limitans interna, ILM), as a result of which a significantly lower recurrence rate can be achieved. The removal of the epiretinal membrane or of the inner limiting membrane is referred to in each case as membrane peeling.

Membrane peeling places high demands on the surgeon. The membrane can be recognized only with difficulty with the aid of conventional microscopes. Therefore, membrane peeling heretofore has been deemed to be the most difficult intervention that is carried out on the eye.

In order to distinguish the membrane from the underlying and surrounding healthy tissue, in conventional interventions use is generally made of a dye which stains tissue structures selectively in the visible spectral range. However, a number of these dyes have been discussed critically with regard to a possible toxicity. The dye must typically be used with the highest possible dilution in order to rule out a toxic effect to the greatest possible extent. An additional factor is laborious handling of the dye in order to selectively colour the desired tissue region. After use, the dye must be washed out in order as far as possible to rule out a situation in which residual amounts remain in the body.

Therefore, there is a need for a system and a method for operating the system for eye examination which allow an effective diagnosis or treatment of epiretinal gliosis.

SUMMARY

Embodiments provide a system for examining an eye. The system comprises a microscopy system for generating an image plane image of an object region. The system can comprise an OCT system, which is configured to acquire OCT data from the object region which reproduce the object region in different stress states. The system can comprise a data processing unit, which is configured to determine at least one value of a stress-dependent parameter, depending on the OCT data. The system can be configured to generate an output image, depending on the image plane image and furthermore depending on the stress-dependent parameter.

A system which allows an efficient examination or treatment of epiretinal gliosis is provided as a result. In particular, the output image generated depending on the stress-dependent parameter enables a more accurate pre- or intraoperative analysis of an epiretinal membrane.

The microscopy system can be designed as a mono or stereo microscopy system. The microscopy system can comprise one observation channel, through which an object plane arranged in the object region can be imaged onto the image plane. The microscope designed as a stereoscopic system can comprise two observation channels, which respectively image the object plane into one of two image planes. The two images generated in the process can represent stereoscopic half-images. The microscopy system can comprise an ophthalamoscopy system and/or an optical reducing system arranged in each case in the observation beam path between an objective of the microscopy system and the eye. The reducing system can comprise one or a plurality of reducing lenses. The ophthalamoscopy system can be arranged between the reducing system and the eye.

The OCT system can be designed to generate an OCT measurement beam. The OCT measurement beam can pass in a focusing manner towards the object region. An axial measurement region of the OCT system can be arranged at least partly in the object region.

The object region can be arranged in a posterior portion of the eye. The object region can comprise at least one part of the retina, at least one part of an epiretinal membrane and/or at least one part of an inner limiting membrane.

The OCT data can comprise an axial scan (A-scan). Alternatively or additionally, the OCT data can comprise a depth cross section (B-scan), a horizontal cross section (C-scan) and/or a volume scan. The depth cross section can be oriented parallel to the axis of the OCT measurement beam. The horizontal cross section can be oriented perpendicular to the axis of the OCT measurement beam.

The stress-dependent parameter can be dependent on a mechanical stress in the object region. In particular, the stress-dependent parameter can be dependent on a mechanical stress in an epiretinal membrane. The stress-dependent parameter can be a local stress-dependent parameter. Values of the local stress-dependent parameter can be dependent on a local stress in the object region. In this context, local can mean that the value of the stress-dependent parameter has a local validity range. The extent of the local validity range can be less than 50 micrometers, less than 20 micrometers, or less than 10 micrometers.

The stress-dependent parameter can be a strain or can be dependent on a strain. The strain can be a local strain. A value of the strain can be positive or negative, that is to say represent a positive or negative change in length. The strain can be an axial strain. In this context, the expression "axial" can mean that the strain is measured along an axis of the OCT measurement beam. Alternatively, the strain can be a lateral strain. In this context, the expression "lateral" can mean that this is the strain relative to a direction which is oriented parallel to a surface tangent of the membrane at the measurement location. Alternatively or additionally, the stress-dependent parameter can be a strain rate or can be dependent on a strain rate. The strain rate can be a local strain rate. The strain rate can be defined as a derivative of the strain with respect to time. The strain rate can be an axial or a lateral strain rate.

Alternatively, the stress-dependent parameter can be an elasticity parameter or can be dependent on an elasticity parameter. The elasticity parameter can be a local elasticity parameter. An elasticity parameter can be, for example: a modulus of elasticity (also referred to as Young's modulus), a shear modulus (also referred to as modulus of rigidity), Poisson's ratio (term denoting ratio of transverse strain to longitudinal strain) or a compression modulus.

The system can be designed to ascertain the stress-dependent parameter by means of OCT elastography (optical coherence tomography elastography, also abbreviated to OCE). OCT elastography can be implementable with the aid of the OCT system and the data processing unit.

In accordance with one embodiment, the system comprises a stress generating device, which is configured to generate the different stress states. A stress state can be defined by a spatial distribution of the mechanical stress in the object region. The stress at a location in the object region can be described by a stress sensor, for example.

The different stress states can be generated by different force actions which act on the object region. The force actions can act on the object region at different points in time. The different stress states can generate different strains, compressions and/or shears in the tissue. One of the stress states can represent a state without force action on the object region. The stress states can be static, quasi-static or dynamic. The stress states can be generated for example by a dynamic, quasi-static and/or static force action being exerted by means of the stress generating device. The stress generating device can touch a tissue region of the eye. By way of example, the stress generating device can comprise a sound transducer and/or an instrument configured to exert a quasi-static or static pressure on the tissue region by touching contact. Alternatively or additionally, the stress generating device can comprise forceps used for plucking the tissue region. The tissue region can comprise, for example, a part of the epiretinal membrane. Alternatively or additionally, the different stress states can be generated by different values of the intraocular pressure. Alternatively or additionally, the stress generating device can be configured for a non-contact force action. By way of example, the stress generating device can be configured to generate the force action by means of an air, gas and/or liquid flow which impinges on a tissue region of the eye, such as the object region.

Quasi-static stress states can be defined by the fact that a change in the stress state takes place more slowly than a measuring time of the OCT system required for detecting the value of the stress-dependent parameter. Alternatively or additionally, the quasi-static stress states can be defined by the fact that an excitation frequency for changing the stress state is less than 50 Hz, or less than 10 Hz, or less than 5 Hz.

Dynamic stress states can be generated by means of a sound wave, in particular by means of an ultrasound wave. The sound wave can be a transverse wave. The sound wave can propagate along the retina and/or along the epiretinal membrane.

The system can be configured such that the output image can be viewed by an observer. The data processing unit can comprise a graphical user interface designed to display the output image. Alternatively or additionally, the system can be designed to generate the output image in the image plane in which the system generates the image plane image of the object region. As a result, the user can view the output image through one or a plurality of eyepieces of the microscopy system.

In accordance with one embodiment, the data processing is furthermore configured to determine the output image depending on a measurement location, or depending on one or a plurality of coordinate values of a measurement location, wherein the stress-dependent parameter was detected at the measurement location. The data processing unit can be configured to determine a region in the output image which corresponds to the measurement location or which substantially corresponds to the measurement location. The region can represent a projection of the measurement location onto the object plane or substantially represent a projection of the measurement location onto the object plane. The data processing unit can be configured to highlight one or a plurality of regions of the output image in a visually recognizable manner. Each of the regions can represent one or a plurality of measurement locations. One or a plurality of values of the stress-dependent parameter may have been determined at each of the measurement locations.

In accordance with one embodiment, the output image comprises a reproduction of at least one part of the image plane image. The data processing unit can be configured to generate the reproduction by means of a colour and/or a grey-scale value coding. The colour and/or grey-scale value coding can be dependent on the value of the stress-dependent parameter.

The microscopy system can comprise an image acquisition sensor. The data processing unit can generate a digital image plane image, which reproduces the image plane image, depending on signals of the image acquisition sensor. The digital image plane image can be a colour reproduction or a grey-scale value reproduction. The colour and/or grey-scale value coding can alter colour and/or grey-scale values of the digital image plane image, depending on the value of the stress-dependent parameter.

Alternatively or additionally, the microscopy system can be designed to generate a second image plane image in the image plane, such that the first image plane image in the image plane is superimposed with the second image plane image. As a result, the output image can be generated in the image plane. The superimposition of the first image plane image with the second image plane image can be observable through eyepieces of the microscopy system. The superimposition of the first image plane image with the second image plane image can generate the colour and/or grey-scale value coding. The microscopy system can comprise a display and an optical unit configured to image an image generated on the display onto the image plane. The display can be an LCD display and/or TFT display, for example. The display can be a backlit display and/or can be transilluminatable with light from a light source.

In accordance with a further embodiment, the data processing unit is configured to generate a graphical representation depending on the value of the stress-dependent parameter. The output image can be generated by means of a superimposition of the graphical representation with at least one part of the image plane image. Therefore, the output image can represent a superimposition of the graphical representation with at least one part of the image plane image. The graphical representation can be dependent on a location in the object region at which the value of the stress-dependent parameter was determined. By way of example, the graphical representation can display in a visually recognizable manner a location in the image plane image which corresponds to the location at which the value of the stress-dependent parameter was determined.

The data processing unit can be designed to superimpose the graphical representation with a digital image plane image, which reproduces the image plane image of the image plane, for the purpose of generating the output image. Alternatively or additionally, the microscopy system can be designed to generate an image of the graphical representation in the image plane, such that a superimposition of the image plane image with the image of the graphical representation can be perceived through eyepieces of the microscopy system.

In accordance with a further embodiment, the stress-dependent parameter is dependent on a stress in a membrane and/or on a stress in an epiretinal membrane of the eye. The stress in the membrane and/or the epiretinal membrane can be a lateral membrane stress. The lateral membrane stress can be defined as a stress relative to a direction which is oriented parallel to a surface tangent of the membrane at the measurement location.

In accordance with a further embodiment, the data processing unit is furthermore configured to detect a location dependence of the stress-dependent parameter. The data processing unit can be configured to generate the output image depending on the location dependence detected. Detecting the location dependence can comprise determining a multiplicity of values of the stress-dependent parameter at a multiplicity of locations within the object region. The output image can be generated depending on the multiplicity of values of the stress-dependent parameter.

In accordance with a further embodiment, the data processing unit is furthermore configured to determine a tissue structure image region, depending on the OCT data. The tissue structure image region can represent at least one part of a tissue structure of the eye, such as, for example, the epiretinal membrane or the inner limiting membrane. The data processing unit can be configured to ascertain the value of the stress-dependent parameter depending on the tissue structure image region determined.

The OCT data can represent an image region which reproduces the scanned region of the object region. The image region can be two-dimensional or three-dimensional. By way of example, the image region can be the two-dimensional region of a depth sectional image which was generated by a depth scan (that is to say a B-scan). Alternatively, the image region can be a three-dimensional region representing a scan volume of a volume scan. The tissue structure image region can lie within the image region. The tissue structure image region can be two-dimensional or three-dimensional.

Determining the tissue structure image region can comprise a segmentation of the OCT data. The segmentation can comprise one or a combination of the following methods: intensity-based segmentation, graph-based segmentation, feature-based segmentation, atlas-based segmentation, model-based segmentation. Additionally or alternatively, the segmentation can be carried out by means of machine learning. Additionally or alternatively, the data processing unit can be configured to carry out a classification of segmented regions.

The data processing unit can be configured to carry out the segmentation and/or the classification in each case automatically and/or user-interactively. By way of example, the system can comprise a graphical user interface configured to display a graphical representation of at least one part of the image region of the OCT data. The user interface can furthermore be designed to receive user inputs with the aid of which the data processing unit determines the tissue structure region.

The data processing unit can be configured to determine the value of the stress-dependent parameter selectively within the tissue structure region or to determine it at a location in the image region which is situated in a predefined spatial relationship with respect to the tissue structure region. The spatial relationship can be determined for example by a maximum distance between the measurement location and the tissue structure region.

In accordance with a further embodiment, the data processing unit is designed to ascertain a parameter of a lateral extent of a tissue structure image region. The parameter can be ascertained depending on the OCT data. The lateral extent can be measured parallel to an object plane of the microscopy system and/or can be measured perpendicular to an axis of a measurement beam of the OCT system in the object region. The data processing unit can be configured to determine the output image depending on the parameter of the lateral extent.

The object plane can be arranged in the object region. The parameter of the lateral extent can be a parameter of a position and/or of a geometry of the lateral extent of the tissue structure image region. The lateral extent can be defined as a projection of the tissue structure image region onto the object plane or onto a plane which is oriented perpendicular to the axis of the measurement beam in the object region. The lateral extent can represent an area. The data processing unit can be configured to determine at least one parameter of a position and/or geometry of the lateral extent or of the area. This parameter therefore represents a parameter of the lateral extent. Alternatively or additionally, the data processing unit can be designed to determine spatial coordinates of an edge of the lateral extent or of the area. A spatial coordinate of the edge therefore represents a parameter of the lateral extent. The output image can be configured such that the lateral extent, the area and/or the edge are/is marked in a visually recognizable manner. The visually recognizable marking can be, for example, a coloured border and/or a colour highlighting of the area.

In accordance with a further embodiment, the system furthermore comprises an instrument configured for manipulating at least one part of the object region. The data processing unit can be configured to determine a value of a supervisory parameter for supervision of the instrument depending on the OCT data. The data processing unit can be configured to determine the output image depending on the value of the supervisory parameter. The output image can be dependent on the determined value of the supervisory parameter.

A supervisory parameter can be, for example, a parameter of a position of an engagement point at which the instrument engages on the object region for a manipulation. Furthermore, a supervisory parameter can be an order of a multiplicity of engagement points, wherein the instrument is brought close to the engagement points in this order in order to carry out a manipulation at each of the engagement points.

The instrument can be configured for examining and/or for treating the object region. The instrument can be at least partly insertable into the interior of the eye, for example by means of an incision. The instrument can be configured for removing at least one partial region of the object region. By way of example, the instrument can be configured for removing the epiretinal membrane and/or the inner limiting membrane. The instrument can comprise forceps, a blade and/or a needle, for example.

The system can be configured to ascertain the value of the supervisory parameter automatically and/or user-interactively. The system can be configured such that at least one position parameter and/or orientation parameter of the instrument can be set in a controllable manner depending on the supervisory parameter. The instrument can be drive-connected to an actuator. The actuator can be signal-connected to a controller. Depending on signals of the controller, at least one parameter of the position and/or of the orientation of the instrument can be settable in a controllable manner.

In accordance with a further embodiment, the data processing unit is configured to determine the value of the supervisory parameter depending on the value of the stress-dependent parameter. By way of example, the supervisory parameter can be configured for positioning of the instrument, such that a partial region of the object region which has a high mechanical stress can be manipulated by the instrument. Additionally or alternatively, the data processing unit can be configured to ascertain the value of the supervisory parameter depending on the tissue structure image region determined and/or depending on the parameter of the lateral extent of the tissue structure region.

In accordance with a further embodiment, the object region comprises at least one part of a retina of the eye and/or at least one part of an epiretinal membrane.

Embodiments provide a system for examining an eye. The system can comprise a data processing unit, which is configured to read in OCT data which were acquired from an object region by means of an OCT system. The object region can comprise at least one part of an epiretinal membrane of the eye. The OCT data can reproduce the object region for different stress states. The data processing unit can furthermore be configured to determine a value of a stress-dependent parameter depending on the OCT data. The stress-dependent parameter can be dependent on a stress of the epiretinal membrane.

In accordance with one embodiment, the data processing unit is furthermore configured to determine a location dependence of the stress-dependent parameter. The location dependence can be determined within the epiretinal membrane. Detecting the location dependence can comprise determining a multiplicity of values of the stress-dependent parameter at a multiplicity of locations within the epiretinal membrane.

In accordance with a further embodiment, the data processing unit is furthermore configured to determine a tissue structure region within an image region of the OCT data. The tissue structure region can be determined depending on the acquired OCT data. The tissue structure region can represent at least one part of the epiretinal membrane. The data processing unit can furthermore be designed to determine the value of the stress-dependent parameter selectively within the tissue structure region determined.

In accordance with a further embodiment, the stress of the epiretinal membrane is a lateral membrane stress of the epiretinal membrane.

In accordance with a further embodiment, the system comprises an OCT system designed for acquiring the OCT data. In accordance with a further embodiment, the system comprises a stress generating device configured to generate the different stress states.

Embodiments provide a method for operating a system. The method can comprise generating an image plane image in an image plane of an object region by means of a microscopy system of the system. The method can furthermore comprise acquiring OCT data from the object region by means of an OCT system of the system. The OCT data can reproduce the object region in different stress states. The method can furthermore comprise determining a value of a stress-dependent parameter by means of a data processing unit of the system, depending on the OCT data. The method can furthermore comprise generating an output image, depending on the determined value of the stress-dependent parameter and depending on the image plane image.

Embodiments provide a method for operating a system. The method can comprise reading in OCT data by means of a data processing unit of the system. The OCT data can be acquired from an object region, wherein the object region reproduces at least one part of an epiretinal membrane of an eye. The OCT data can reproduce the object region for different stress states. The method can furthermore comprise determining a value of a stress-dependent parameter by means of the data processing unit, depending on the OCT data. The stress-dependent parameter can be dependent on a stress of the epiretinal membrane.

Embodiments provide a computer program product, comprising computer-readable instructions which, when loaded into the memory of a computer and/or computer network and executed by a computer and/or computer network, have the effect that the computer and/or the computer network perform(s) a method in accordance with one of the above embodiments.

BRIEF DESCRIPTION OF THE FIGURES

The above features and further features of the present disclosure will be explained by the following detailed description of the exemplary embodiments with reference to the accompanying drawings. It is emphasized that not all possible embodiments of the present disclosure necessarily afford all or some of the advantages indicated here.

DETAILED DESCRIPTION OF EXEMPLARY EMBODIMENTS

Figure 1:
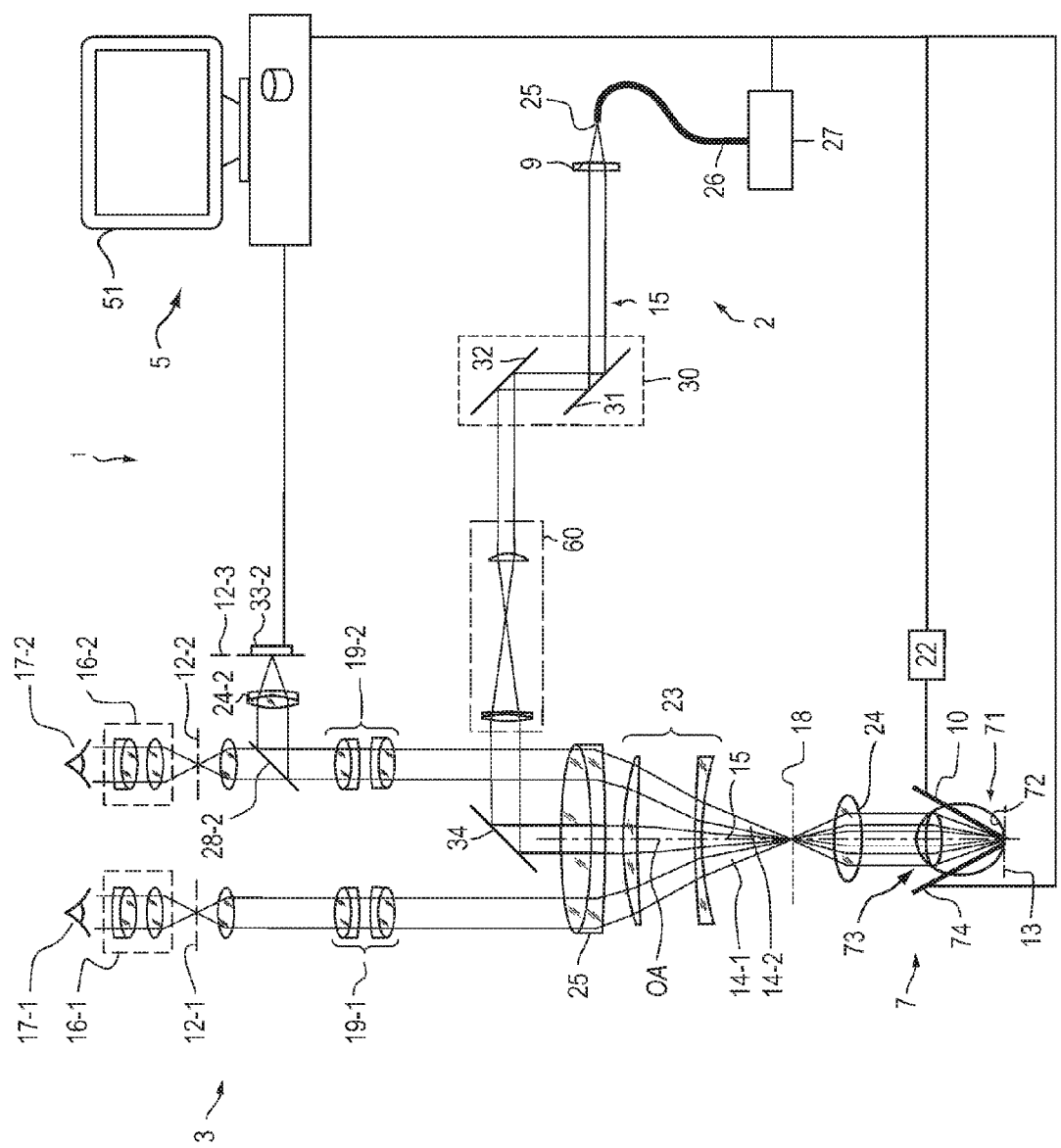
FIG. 1 shows a system for imaging a region of a posterior portion of the eye in accordance with one exemplary embodiment.

FIG. 1 is a schematic illustration of a system 1 for imaging an object region of an eye 7 in accordance with one exemplary embodiment. The object region is situated in a posterior portion 71 of the eye 7 and comprises a part of the retina 72.

The system 1 comprises a microscopy system 3 and an OCT system 2. The microscopy system 3 is configured as a stereo microscopy system comprising two observation channels 14-1, 14-2, which respectively image an object plane 13 into one of two stereoscopic image planes 12-1, 12-2. However, it is also conceivable for the microscopy system 3 to be configured as a monoscopic microscope.

The stereoscopic microscopy system 3 is configured such that light beams of the observation channels 14-1 and 14-2 which proceed in each case from a point in the object plane 13 pass through the anterior portion 73 of the eye 7, an opththalmoscopy system 24, a reducing system 23 and the objective 25. An intermediate focus 18 is situated between opththalmoscopy system 24 and reducing system 23, said intermediate focus being optically conjugate with respect to the object plane 13 and with respect to the image planes 12-1, 12-2. The reducing system 23 can comprise one or a plurality of reducing lenses. The light beams leave the objective 25 as substantially parallel light beams. After leaving the objective 25, the light beams pass through a zoom system 19-1 of the observation channel 14-1 or a zoom system 19-2 of the observation channel 14-2. A magnification of the image generation in the stereoscopic image planes 12-1 and 12-2 can be set by means of the zoom systems 19-1, 19-2.

The system 1 furthermore comprises a respective eyepiece 16-1, 16-2 for each of the observation channels 14-1, 14-2. The eyepieces 16-1 and 16-2 are configured such that for a user the images in the image planes 12-1, 12-2 can be viewed by the eyes 17-1, 17-2 through the eyepieces 16-1, 16-2.

The microscopy system furthermore comprises a beam splitter 28-2, which is configured to couple out light from the observation channel 14-2. Via a focusing optical unit 24-2, the coupled-out light is imaged onto an image acquisition sensor 33-2 arranged in an image plane 12-3. The image plane 12-3 is optically conjugated with respect to the object plane 13. A data processing unit 5 is signal-connected to the image acquisition sensor 33-2 and designed to generate a digital image plane image, depending on the signals of the image acquisition sensor 33-2. As will be described in detail with reference to FIGS. 6 and 7, the data processing unit 5 generates an output image depending on the digital image plane image. The output image is generated depending on the digital image plane image and furthermore depending on a stress-dependent parameter that is dependent on a mechanical stress in the object region. The stress-dependent parameter is determined depending on OCT data which are acquired by means of the OCT system 2. It has been found that it is thereby possible to carry out an efficient examination and/or treatment of epiretinal gliosis (also referred to as macular pucker).

The OCT system 2 is configured to generate a measurement beam 15 that is guided along a measuring arm to the posterior portion 71 of the eye 7. The light of the measurement beam 15 is generated by a light source within an OCT unit 27 and is fed into an optical waveguide 26. From an end 25 of the optical waveguide 26, the measurement beam 15 is emitted into the OCT measurement beam optical unit. The OCT measurement beam optical unit guides the measurement beam 15 to the eye 7. After emerging from the optical waveguide 26, the measurement beam 15 passes successively through a collimation optical unit 9, a scan unit 30, comprising two scan mirrors 31, 32, and a beam expander 60, which is configured as a Kepler telescope. After leaving the beam expander 60, the measurement beam 15 impinges on a deflection element 34, by which the measurement beam 15 is directed onto the objective 25. The measurement beam optical unit is configured in such a way that the measurement beam 15 is incident on the objective 25 as a substantially parallel beam. The measurement beam 15 passes through the objective 25, the reducing system 23, the ophthalmoscopy system 24, the anterior portion 73 of the eye and passes in a focusing manner towards the posterior portion 71 of the eye. In the posterior portion 71 of the eye 7, the measurement beam 15 forms a measurement focus, wherein a part of the epiretinal membrane and a part of the retina 72 are situated within the axial measurement region of the OCT system 2.

The system 1 can be used to examine an epiretinal membrane and the inner limiting membrane of the retina 72 and/or to remove them from the retina 72.

Figure 2A:
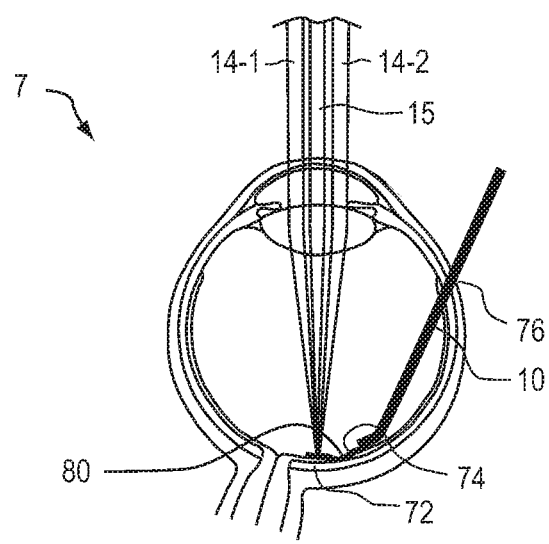
FIG. 2A is a schematic illustration of the removal of an epiretinal membrane and/or of the inner limiting membrane.

FIG. 2A is a schematic illustration of the eye 7 during a treatment of epiretinal gliosis. In epiretinal gliosis, an epiretinal membrane 74 forms on the central region of the retina 72. The central region is referred to as the macular and comprises the fovea centralis 80. In the course of the disease, the epiretinal membrane 74 contracts, such that wrinkles form in the underlying retina 72. This is described in detail further below with reference to FIG. 2B.

For the treatment of epiretinal gliosis, the epiretinal membrane 74 is removed by means of an instrument, such as intraocular forceps 10, for example, such that the wrinkles can regress from the retina 72. The intraocular forceps 10 are inserted into the vitreous humour through an incision 76 situated in the sclera of the eye 7. The surgeon can use the intraocular forceps 10 to grip the epiretinal membrane 74 successively at engagement points situated on the edge of the membrane. At each of the engagement points, a movement is carried out in a direction which is oriented substantially tangentially with respect to the surface of the epiretinal membrane 74. Alternatively or additionally, the surgeon can use other instruments, such as a needle or a blade. By additionally detaching the inner limiting membrane (not shown in FIG. 2A), which represents the outermost layer of tissue of the retina 72 towards the interior of the eye, it is possible to achieve a reduced regression rate.

Figure 2B:
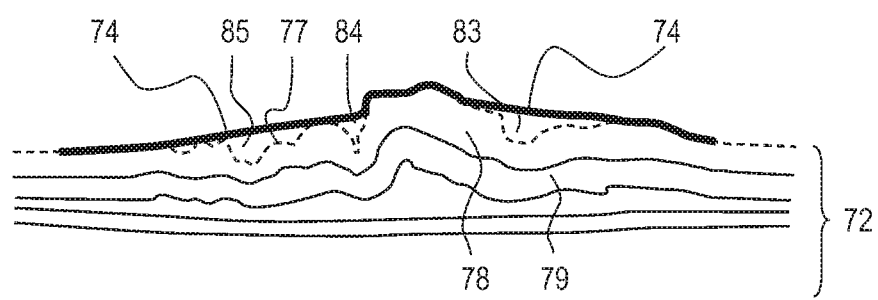
FIG. 2B is a schematic sectional illustration of the epiretinal membrane and of the upper retinal layers in the eye illustrated in FIG. 2A.

FIG. 2B is a schematic illustration of an OCT B-scan which was obtained using the OCT system 2 illustrated in FIG. 1. The epiretinal membrane 74 is regionally attached to the inner limiting membrane 77 of the retina 72. The inner limiting membrane 77 is illustrated by dashed lines in FIG. 2B. In a healthy eye, the inner limiting membrane 77 constitutes the topmost layer of the retina and is in contact with the vitreous humour. The epiretinal membrane 74 contracts the topmost layers 77, 78, 79 of the retina 72 in such a way that the latter form wrinkles 83, 84 and 85. The wrinkled structure of the retina 72 results in distorted vision for the patient. The mechanical forces exerted on the tissue of the retina 72 additionally lead to an accumulation of water, which causes a swelling of the retina (macular oedema). This additionally reduces the central field of vision.

Figure 3:
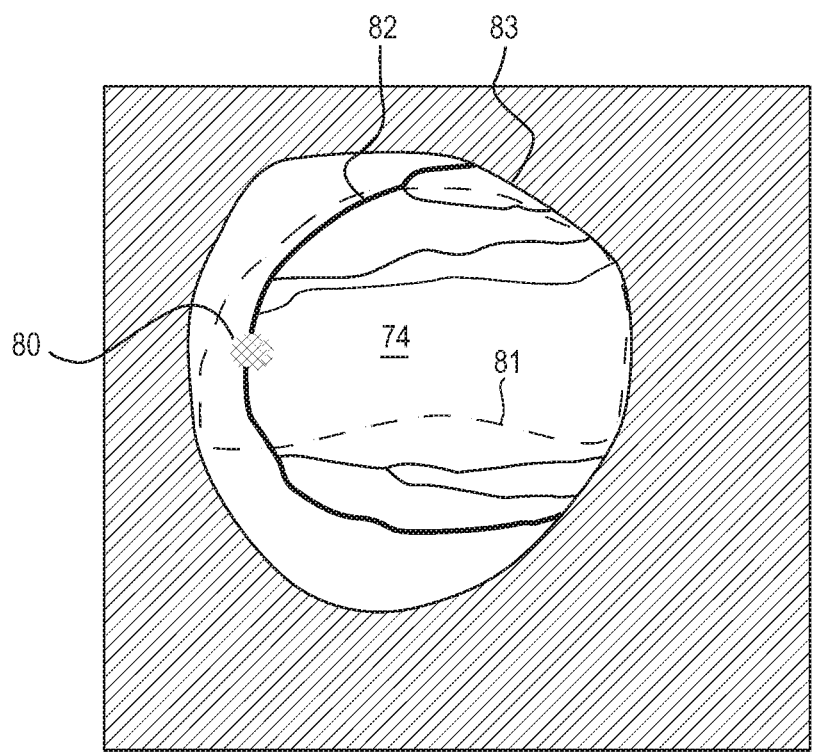
FIG. 3 is a schematic illustration of an image plane image of the fundus of the eye which was generated by means of the microscopy system of the exemplary embodiment shown in FIG. 1.

FIG. 3 is a schematic illustration of an image plane image which was generated in one of the image planes 12-1, 12-2 and 12-3 (shown in FIG. 1). The fovea centralis 80 and the retinal blood vessels 82 can be discerned within the illuminated region 83 of the object region. The epiretinal membrane 74 is substantially transparent in the visible wavelength range. Therefore, the edge 81 of the epiretinal membrane 74, on which edge the intraocular forceps are intended to engage, can be discerned only with difficulty in the microscope image. A dye that selectively stains the epiretinal membrane 74 is therefore used in conventional methods.

For the following reasons, however, it is desirable to avoid the use of dyes. Many of the dyes are under discussion with regard to a possible toxicity, especially since the dyes can often diffuse through tissue. Therefore, it is generally recommendable to use only a minimum amount of dye in order to minimize the toxic effects. An additional factor often is laborious handling of the dye in order to achieve a selective staining of the epiretinal membrane or of the inner limiting membrane with the dye. After the intervention, the residues of the dye have to be removed again by being rinsed out, in order to prevent residual amounts of the dye from remaining in the body for a relatively long time.

If the surgeon's actions during the removal of the epiretinal membrane or the inner limiting membrane are unfavourable, for example because the spatial region of the membrane cannot be discerned clearly enough in the microscope image, this can have the effect that the membrane often fragments during detachment. However, frequent fragmenting increases the risk of residues of the membrane remaining in the interior of the eye. Such remaining residues can result in the macular pucker growing back.

Moreover, when the recognisability of the epiretinal membrane is deficient, the intervention can result in injuries to the retina, such as tears, for example. These injuries then have to be treated afterwards using an endolaser or by means of cryopexy, for example, in order to prevent a later retinal detachment (amotio retinae).

It has been found, however, that a more precise and toxicologically safe removal of the epiretinal membrane is possible if output images are generated which are dependent on the image plane image in at least one of the image planes 12-1, 12-2, 12-3 (shown in FIG. 1) and furthermore on values of a stress-dependent parameter which are determined depending on OCT data. In the exemplary embodiment shown in FIG. 1, a digital image plane image is generated by the data processing unit 5, depending on signals of the image acquisition sensor 33-2. The output image is generated depending on the digital image plane image and furthermore depending on values of a stress-dependent parameter which are determined depending on the OCT data. Additionally or alternatively, it is conceivable for the system to be configured to generate a second image plane image in at least one of the image planes 12-1, 12-2. The second image plane image is generated depending on the values of the stress-dependent parameter. In said image plane, a superimposition of the first image plane image, which arises as a result of the imaging of the object plane 13, with the second image plane image, which is generated depending on the values of the stress-dependent parameter, arises as a result. It is thereby possible for the surgeon to view the output image by the eyes 17-1, 17-2 through the eyepieces 16-1, 16-2.

The stress-dependent parameter is dependent on a mechanical stress in the object region, in particular on a mechanical stress in the epiretinal membrane. The stress-dependent parameter is determined depending on OCT data which are acquired for different stress states of the object region. As explained in greater detail in the following sections, the different stress states can be dynamic, quasi-static or static.

The dynamic stress states can be generated for example by means of a sound wave, in particular by acoustic radiation force (ARF). The sound wave can be an ultrasound wave. The frequency of the ultrasound wave can be 20 MHz, for example. The sound wave can be generated in wave packets. The wave packets can have for example a duration of 400 microseconds. The system can comprise one or a plurality of needle sound transducers 74 (shown in FIG. 1), which can be inserted into the interior of the eye and can be arranged in such a way that sound waves can be excited in the epiretinal membrane 74 (shown in FIG. 2B) and in the underlying retinal tissue. The needle sound transducer 74 therefore represents a stress generating device. It has been found that transverse waves can thereby be generated in the epiretinal membrane and in the underlying retinal tissue.

The data processing unit can be configured in such a way that a local strain rate generated locally by the sound wave can be determined. The local strain rate is dependent on the stress and is therefore a stress-dependent parameter. The local strain rate can be defined as a derivative of the local strain with respect to time. The local strain rate can be measured along an axis of the measurement beam, that is to say can represent the change over time in the local strain along the axis of the measurement beam. The local strain rate is then referred to as axial local strain rate. Alternatively or additionally, the local strain rate can represent a lateral local strain rate of the epiretinal membrane. The lateral strain rate of the epiretinal membrane can be defined as a strain rate which is relative to a direction oriented parallel to a surface tangent of the epiretinal membrane at the measurement location. The determination of local strain rates by means of OCT elastography is described in the article "In vivo three-dimensional optical coherence elastography" by Brendan F. Kennedy et al., published in OPTICS EXPRESS, Vol. 19, No. 7, pages 6623-6634, the content of which is part of the present disclosure by reference. It has been found that the local strain rate is dependent on the lateral membrane stress of the epiretinal membrane. In particular, it has been found that a higher absolute value of an axial and/or lateral local strain rate means a lower lateral membrane stress. The lateral membrane stress can be defined as a stress relative to a direction which is oriented parallel to a surface tangent of the membrane at the measurement location.

Alternatively or additionally, the data processing unit can be configured in such a way that a local propagation velocity of the sound wave can be determined, depending on the OCT data. The local propagation velocity can relate to a partial region of the object region, such as, for example, to a partial region of the epiretinal membrane or a partial region of the inner limiting membrane. The local propagation velocity is dependent on the local modulus of rigidity. Therefore, the local propagation velocity constitutes a stress-dependent parameter. A measurement for ascertaining local propagation velocities of transverse waves by means of OCT is described for example in the article "Optical Coherence Tomography detection of shear wave propagation in layered tissue equivalent phantoms" by M. Razani et al., published in Proc. of SPIE Vol. 8565 856540-1, the content of which is part of the present disclosure by reference. It has been found that the propagation velocity of the transverse waves in the epiretinal membrane is dependent on the lateral membrane stress in the epiretinal membrane. In particular, it has been found that a higher propagation velocity means a higher lateral membrane stress.

Alternatively, the dynamic stress states can be generated by a low-frequency vibration. The frequency of the low-frequency vibration can be in a range of between 50 and 1000 Hz, for example. The low-frequency vibration can be generated by a sound transducer, for example by the needle sound transducer 74 illustrated in FIG. 1. Depending on OCT data which were measured upon an excitation of the object region with low-frequency vibrations, the local strain rate can be determined. The use of low-frequency vibrations for elastography is described in the article "Selected Methods for Imaging Elastic Properties of Biological Tissues" by James F. Greenleaf et al. published in the Annual Review of Biomedical Engineering 2003, 5, pages 57 to 78, the content of which is part of the present disclosure by reference.

Alternatively, the stress states can be quasi-static. A quasi-static stress state can be defined by the fact that the alteration of the stress state is slow in comparison with the measurement time of a scan of the OCT system, that is to say, for example, of an A-scan, of a B-scan or of a C-scan. The quasi-static excitation can take place for example at a frequency which is less than 100 Hz, or less than 50 Hz, or less than 10 Hz, or less than 5 Hz. The excitation vibration can be generated by a sound transducer, for example by the needle sound transducer 74 illustrated in FIG. 1. Depending on the OCT data which were acquired for the quasi-static stress states, the local strain can be determined. The local strain can be an axial local strain, that is to say measured along an axis of the measurement beam. Alternatively, the local strain can represent a lateral local strain of the epiretinal membrane. The lateral local strain of the epiretinal membrane can be defined as a strain relative to a direction which is oriented parallel to a surface tangent of the epiretinal membrane at the measurement location. The local strain is dependent on the stress and is therefore a stress-dependent parameter. It has been found that the local strain is dependent on a lateral membrane stress of the epiretinal membrane. In particular, it has been found that a higher absolute value of the local strain means a low lateral membrane stress. The determination of the local axial and lateral strain is explained in more detail with reference to FIGS. 4A and 4B.

Alternatively, the stress states can be static. Static stress states can be generated, for example, by an alteration of the intraocular pressure and/or by a force that is constant over time being exerted with the aid of an instrument. The instrument can be operable automatically and/or manually. The instrument can be forceps, for example. The user can use the forceps to grip a region of the epiretinal membrane, for example, and can alter the stress state of the object region by plucking. Alternatively or additionally, the user can press the epiretinal membrane against the retina using an instrument. The strain in a tissue region which is generated by the alteration of the intraocular pressure and/or by the exertion of the force that is constant over time is dependent on the stress in the tissue region and is therefore a stress-dependent parameter. Depending on OCT data which were acquired for the static stress states, the local axial strain and/or the local lateral strain can be determined.

Figure 4B:
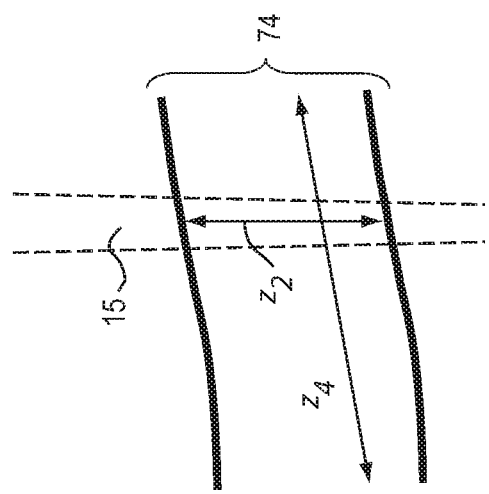
FIGS. 4A and 4B are a schematic illustration of the determination of local axial or local lateral strains in the epiretinal membrane depending on OCT data, wherein the OCT data were determined by means of the OCT system shown in FIG. 1.
Figure 4A:
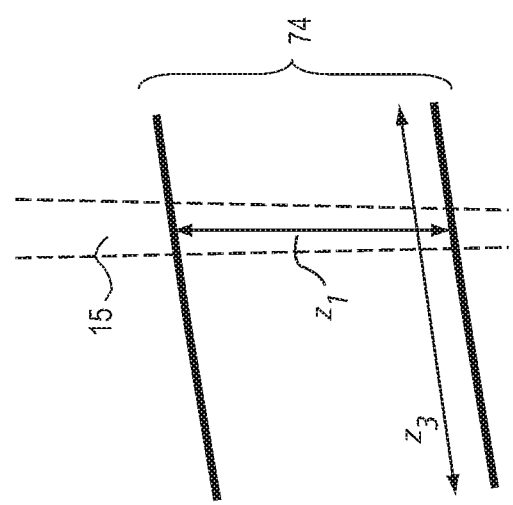

FIGS. 4A and 4B illustrate the determination of the local axial strain and the determination of the local lateral strain depending on the OCT data. FIG. 4A shows a region of the epiretinal membrane 74 in a first stress state; FIG. 4B shows the same region of the epiretinal membrane 74 in a second stress state. One of the two stress states can be a state in which no force is exerted on the object region.

In the first stress state, as illustrated in FIG. 4A, the epiretinal membrane has the thickness $z_1$, indicated by a double-headed arrow. As illustrated in FIG. 4B, in the second stress state, the same region of the epiretinal membrane has the thickness $z_2$, likewise indicated by a double-headed arrow. Depending on the measured thicknesses for the two stress states, the local axial strain $\epsilon_{axial}$ can be calculated, which reproduces the strain in the region of the membrane measured along the axis of the measurement beam 15:

$$\epsilon_{axial} = \frac{z_2 - z_1}{z_1}$$

Instead of the entire thickness of the epiretinal membrane, it is also possible to use an axial length of a part of the epiretinal membrane for ascertaining the axial local strain.

The local lateral strain can be determined in an analogous manner. In the first stress state, the region of the epiretinal membrane 74 has the lateral length $z_3$, wherein said lateral length is measured in a direction which is oriented parallel or substantially parallel to a surface tangent of the epiretinal membrane 74 in the first state at the measurement location. In the second stress state, the same region has the lateral length $z_4$, wherein said lateral length is measured in a direction which is parallel or substantially parallel to a surface tangent of the epiretinal membrane 74 in the second state at the measurement location. In the case of slight deformations of the object region, the directions of the surface tangents of the epiretinal membrane 74 can be approximately identical in the first and second states.

Depending on the measured lateral lengths, the local lateral strain $\epsilon_{lateral}$ can be calculated in accordance with the following relationship:

$$\epsilon_{lateral} = \frac{z_4 - z_3}{z_3}$$

The local lateral strain can be direction-dependent, i.e. dependent on the direction along which the lateral lengths $z_3$ and $z_4$ are measured. By way of example, in the example shown in FIGS. 4A and 4B, the lateral strain in a plane which is oriented perpendicular to the plane of the drawing in FIGS. 4A and 4B can be different from the lateral strain in a plane which is oriented parallel to the plane of the drawing.

Depending on measurements of the local lateral strain in different directions, it is possible to determine a direction of the maximum lateral membrane stress. It has been found that a smaller absolute value of the lateral strain means a larger lateral membrane stress. Therefore, the direction of the maximum lateral membrane stress is generally a direction of the minimum absolute value of the lateral strain. Stress lines can be calculated depending on the direction of the maximum lateral membrane stress. A tangential direction of the stress line can be assigned to each location on the stress line, wherein the tangential direction indicates the direction of the maximum lateral membrane stress at the location.

The stress lines can additionally or alternatively generate depending on biomechanical models, in particular atlas-based biomechanical models. The biomechanical models can be generated depending on the OCT data. In order to generate the biomechanical models, the OCT data can be segmented in order to identify the epiretinal membrane and/or further tissue structures.

The data processing unit 5 (shown in FIG. 1) is designed to determine the local strain using a speckle tracking method and/or using a cross-correlation method. These methods make it possible, for different stress states, to determine the membrane thickness ($z_1$ and $z_2$ in FIGS. 4A and 4B) and/or the lateral length of an examined region ($z_3$ and $z_4$ in FIGS. 4A and 4B). Alternatively or additionally, the data processing unit can be designed to determine the local strain, in particular the axial local strain, with the aid of a phase-sensitive OCE measuring method (Optical Coherence Elastography). This method is explained in the next sections.

In the case of a frequency domain OCT system, the light backscattered from an axial measurement region is decomposed into a spectrum. The application of an inverse Fourier transformation to this spectrum yields a complex-valued signal. The absolute values of said signal represent the intensity of the backscattered light at different measurement depths. The phases of the signal represent the phases of the backscattered light at the different measurement depths.

An axial movement of partial regions of the object region along the axes of the measurement beam of the OCT system produces a phase shift between the OCT signals. Therefore, by ascertaining the phase difference $\Delta\theta$ between two A- or B-scans, it is possible to determine the axial movement $\Delta z$ by means of the relationship $$\Delta z = \frac{\Delta\theta}{4\pi n},$$

wherein $\lambda$ is the central wavelength of the OCT measurement light and n is the refractive index of the partial region from which the light of the measurement beam is backscattered.

It has been found that the absolute value of the local strain, the absolute value of the local strain rate and/or the local propagation velocity are/is in each case a measure of the lateral membrane stress of the epiretinal membrane. In this case, these stress-dependent parameters can be measured within the epiretinal membrane. Alternatively or additionally, it is possible to measure these stress-dependent parameters in a region which does not exceed a predefined maximum distance from the epiretinal membrane. As has already been described above with reference to FIGS. 4A and 4B, it has furthermore been shown that it is possible to determine stress lines depending on the measurement of the local lateral strain.

Therefore, it is possible, depending on one or a plurality of said stress-dependent parameters, to configure the output image in such a way that the user can visually recognize at what locations high lateral membrane stresses are present in the epiretinal membrane and how the stress lines of the lateral membrane stress proceed.

In order to determine the values of the local stress-dependent parameter within the epiretinal membrane or within a region which is at a distance from the epiretinal membrane that is less than a predefined maximum distance, the data processing unit is designed to carry out a segmentation of the OCT data. The segmentation can be configured in such a way that the epiretinal membrane, the inner limiting membrane and/or retinal layers are identified.

The segmentation can comprise for example one or a combination of the following methods: intensity-based segmentation, graph-based segmentation, feature-based segmentation, atlas-based segmentation, and/or model-based segmentation. Additionally or alternatively, the data processing unit can be configured to carry out the segmentation by means of machine learning. The data processing unit can be configured to carry out the segmentation automatically and/or user-interactively. Additionally or alternatively, the data processing unit can be configured to carry out a neighbourhood analysis, depending on the OCT data. The neighbourhood analysis can be a "connected components" method, for example. Additionally or alternatively, the data processing unit can be designed to carry out a classification. The data processing unit can be configured to carry out the neighbourhood analysis and/or the classification automatically and/or user-interactively.

By use of the segmentation, the neighbourhood analysis and/or the classification, those pixels and/or voxels of the OCT data which reproduce the epiretinal membrane can be determined. Therefore, said pixels and/or voxels form a tissue structure image region representing the epiretinal membrane. The tissue structure image region is therefore a partial region of the image region of the OCT data which reproduces the scanned region. Additionally or alternatively, those pixels or voxels of the OCT data which belong to an identical tissue structure can be combined to form a continuous spatial region with the aid of the neighbourhood analysis.

Figure 5:
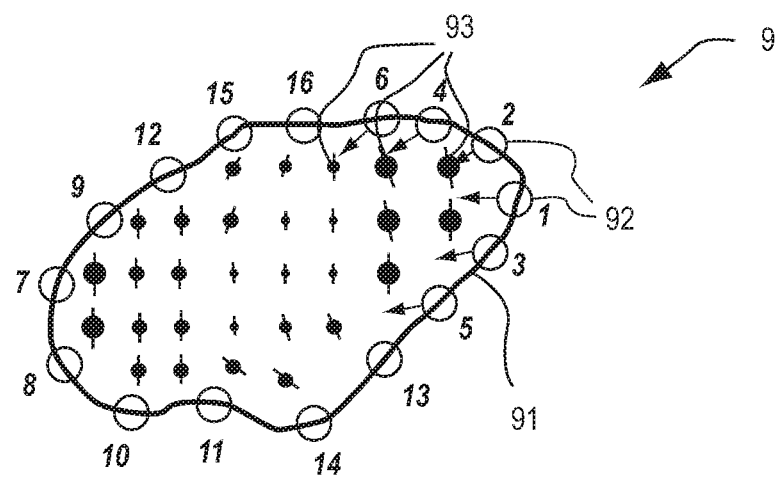
FIG. 5 is a schematic illustration of a graphical representation generated depending on OCT data, wherein the OCT data were generated by means of the OCT system shown in FIG. 1.

FIG. 5 shows a graphical representation 9 which was generated by the data processing unit 5 (shown in FIG. 1) depending on the OCT data. As described further below with reference to FIG. 6, said graphical representation 9 is superimposed on the image plane image (shown in FIG. 3). An output image which can be used for efficiently analysing the epiretinal membrane is generated as a result of the superimposition. The graphical representation 9 has a multiplicity of local stress indicators 93. Each of the local stress indicators 93 was determined depending on at least one value of a stress-dependent parameter, which were determined at one or a plurality of measurement locations. Each of the local stress indicators highlights a respective region of the output image in a visually recognizable manner. For each of the local stress indicators, the respective region substantially represents those measurement locations at which were acquired those values of the stress-dependent parameters depending on which the respective stress-dependent parameter was determined.

For this purpose, the data processing unit ascertains for each of the local stress indicators a region in the output image which represents one or a plurality of measurement locations. In this case, the measurement locations are those measurement locations at which were acquired those values of the stress-dependent parameters depending on which the respective local stress indicator was determined. The graphical representation is therefore dependent on the measurement locations at which the values of the stress-dependent parameters were determined.

Each of the local stress indicators 93 is configured to indicate a size and an orientation in a visually recognizable manner. The size and/or orientation are/is determined depending on the values of the stress-dependent parameters. In the exemplary embodiment illustrated by way of example in FIG. 5, each of the stress indicators 93 has a dot and a line. The orientation of the line indicates the direction of the highest local lateral membrane stress. This is that direction along which the lowest absolute value of the local lateral strain was measured. A larger dot represents a larger lateral membrane stress, relative to the direction of the highest local lateral membrane stress.

Depending on the local stress indicators 93 illustrated, therefore, the surgeon can reliably detach the epiretinal membrane from the retina. By way of example, the surgeon can firstly detach the epiretinal membrane at that location where high lateral membrane stresses are present. In this case, the surgeon can choose a plucking direction which is as far as possible not oriented along the stress line, in order as far as possible not to increase the lateral membrane stresses that occur during plucking in such a way that the membrane tears.

In the example shown in FIG. 5, high lateral membrane stresses occur in that partial region of the object region which is represented by the right-hand side of the graphical representation By detaching the membrane firstly at said partial region, the surgeon can achieve the effect that the high lateral membrane stress occurring in said partial region is largely reduced as early as in the initial steps. The risk of the epiretinal membrane frequently fragmenting in the subsequent steps is reduced as a result.

The graphical representation furthermore has a boundary marking 91 representing the lateral extent of the epiretinal membrane 74 (shown in FIG. 2B). The boundary marking 91 was determined depending on the OCT data. In particular, the boundary marking 91 was determined depending on the tissue structure region which reproduces the epiretinal membrane and which was determined by the segmentation of the OCT data. The projection of said tissue structure region onto a plane produces an area representing the lateral extent of the epiretinal membrane. The plane can be oriented parallel to the object plane 13 (shown in FIG. 1) and/or can be oriented perpendicular to the optical axis of the measurement beam in the object region. The boundary marking 91 thereby highlights in a visually recognizable manner that lateral region over which the epiretinal membrane extends. The surgeon can therefore determine, depending on the output image, at what locations he must engage using the instrument in order to detach as far as possible the entire epiretinal membrane.

The graphical representation 9 shown in FIG. 5 furthermore has engagement point markings 92 arranged in a distributed manner on the boundary marking 91. The engagement point markings 92 mark those points on the epiretinal membrane at which the intraocular forceps 10 (shown in FIG. 1) are intended to engage in order subsequently to pull the epiretinal membrane 74 away from the retina by means of a tensile force in a direction which is oriented substantially tangentially with respect to the surface of the epiretinal membrane 74. The spatial arrangement of the engagement point markings 92 can be ascertained automatically and/or user-interactively. By way of example, the data processing unit can be configured to distribute the engagement point markings 92 uniformly on the boundary marking 91. Additionally or alternatively, the data processing unit can be configured to establish narrower distances between the engagement point markings 92 at those locations at which high lateral membrane stresses occur. Therefore, the data processing unit can be configured to determine the engagement point markings 92 depending on the values of the stress-dependent parameter. Additionally or alternatively, a graphical user interface of the data processing unit can be designed such that the user can define and/or alter the positions of the engagement point markings 92 on the boundary marking 91.

In the graphical representation 9 illustrated in FIG. 5, the engagement point markings 92 are numbered in order to predefine an order according to which the intraocular forceps (shown in FIG. 1) are intended to engage on the epiretinal membrane. The numbers are illustrated in italics in FIG. 5 in order to distinguish them from the reference signs in FIG. 5. The system can be designed such that, depending on the lateral position of the engagement points determined and the order predefined by the numbering, the data processing unit drives an actuator 22 (shown in FIG. 1), said actuator being drive-connected to the intraocular forceps 10, in order to position a distal end of the intraocular forceps 10 relative to the respective engagement points according to the predefined order. Additionally or alternatively, the positioning can be carried out user-interactively. In this case, the user can be oriented by means of the graphical representation 9. Consequently, the graphical representation 9 is generated depending on values of a plurality of supervisory parameters, wherein the supervisory parameters and/or the representation 9 can be used for the user-interactive and/or automatic control of the intraocular forceps 10. In the exemplary embodiment illustrated, the supervisory parameters are the positions and the order—predefined by the numbering—of the engagement points.

The data processing unit can be designed to determine the order of the engagement points automatically and/or user-interactively. The user interface of the data processing unit can be designed such that the user can define and/or alter the order of the engagement points user-interactively via the graphical user interface. The order of the engagement points can be ascertained depending on the values of the stress-dependent parameter. By way of example, the data processing unit can be designed to determine the position and/or the order of the engagement points in such a way that the epiretinal membrane is firstly detached at locations at which high lateral membrane stresses are present. In the graphical representation 9 reproduced in FIG. 5, for example, the engagement point markings 92 on the right-hand side are provided with low numbers since high lateral membrane stresses occur in the right-hand region, as can be discerned from the size of the local stress indicators 93.

The position and/or the order of the engagement point markings 92 can furthermore be ascertained, automatically and/or user-interactively depending on the structure of the underlying retinal layers. By way of example, in the graphical representation reproduced in FIG. 5, on the left-hand side the engagement points are arranged at a greater distance from the fovea centralis 80 (shown in FIG. 3) in order to reduce the risk of damage to the sensitive region of the fovea centralis 80.

The data processing unit is furthermore designed to ascertain a plucking direction for at least one portion of the engagement points. The graphical representation can be generated depending on the plucking directions determined. In the exemplary embodiment illustrated in FIG. 5, the plucking directions are indicated as arrows at the detachment points 1 to 6. In the exemplary embodiment illustrated in FIG. 5, the plucking directions are indicated at the detachment points 1 to 6. The plucking direction can be ascertained such that the probability of a fragmentation of the membrane is reduced to the greatest possible extent. The plucking direction can be ascertained automatically and/or user-interactively.

Alternatively or additionally, ascertaining the position of the engagement points, the order of the engagement points and/or the plucking directions, comprise determining a minimum of an energy functional for different stages of the detachment process. For each of the stages, depending on the boundary conditions of the respective stage, the spatial structure of the epiretinal membrane and/or stress values in the epiretinal membrane can be determined by the minimization of the energy functional. Depending on the stress values determined, it is possible to ascertain whether an increased probability of tearing of the epiretinal membrane occurs during the detachment process. Furthermore, it is thereby possible to simulate how the position of the engagement points, the order of the engagement points and/or the plucking directions at the engagement points are intended to be ascertained, such that the number of plucking locations is minimized, such that the number of plucking processes is minimized, such that the plucking counter to the forces having an advance effect is minimized, and/or such that the plucking is carried out at locations which are at at least a minimum distance from sensitive anatomical tissue structures, such as the fovea centralis 80 (shown in FIG. 3). Additionally or alternatively, expert knowledge can influence the ascertainment of the energy functional. By way of example, it is possible to predefine the fact that the epiretinal membrane is as far as possible firstly detached at all edges before it is pulled away from the retina by a plucking process. As a further example of expert knowledge it is conceivable for behaviour and/or ways of working on the part of the surgeon from previous interventions to be learned from the images automatically by algorithms. It is thereby possible to include for example personal preferences and/or typical ways of working on the part of the surgeon in the optimization.

Figure 6:
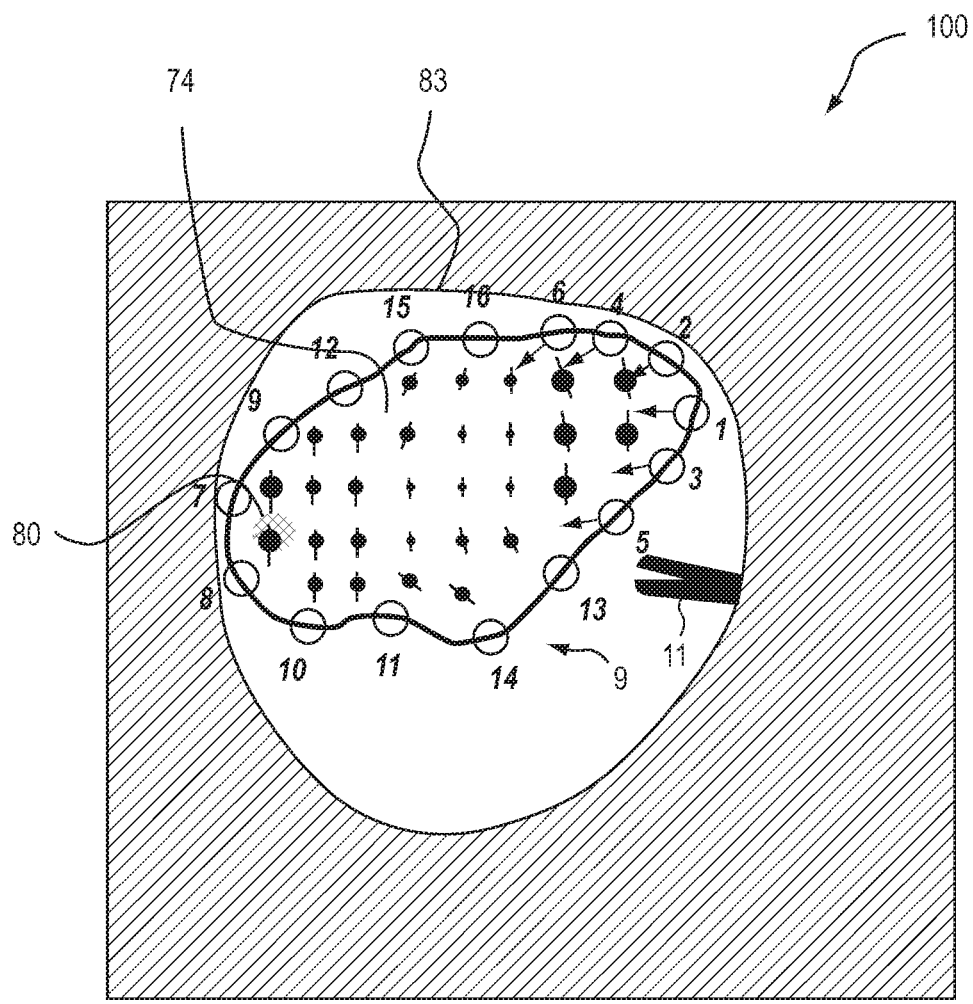
FIG. 6 is a schematic illustration of an output image in which a microscope image is superimposed with the graphical representation shown in FIG. 5.

FIG. 6 is a schematic illustration of the output image 100 generated by the data processing unit, depending on the graphical representation 9 shown in FIG. 5 and furthermore depending on a digital image acquired by means of the image acquisition sensor 33-2. For simplification, the retinal blood vessels are not illustrated in FIG. 6. The output image 100 is displayed on the display 51 (shown in FIG. 1) of the data processing system 5. A projection of the distal end 11 of the intraocular forceps can additionally be seen in the output image 100. Depending on the output image 100, the surgeon can navigate the distal end 11 of the intraocular forceps to the marked engagement points according to the predefined order in order to pluck the epiretinal membrane 74 away at the corresponding location.

It has been found that the marking of the position and the order of the engagement points in the graphical representation 9, and the indication of the plucking directions are advantageous since the surgeon, during the intervention, can immediately recognize the planned sequence of the intervention. Therefore, the surgeon need not carry out any time-consuming analyses of the microscope data or OCT data during the intervention, but rather can concentrate on handling the instrument during the intervention.

Figure 7:
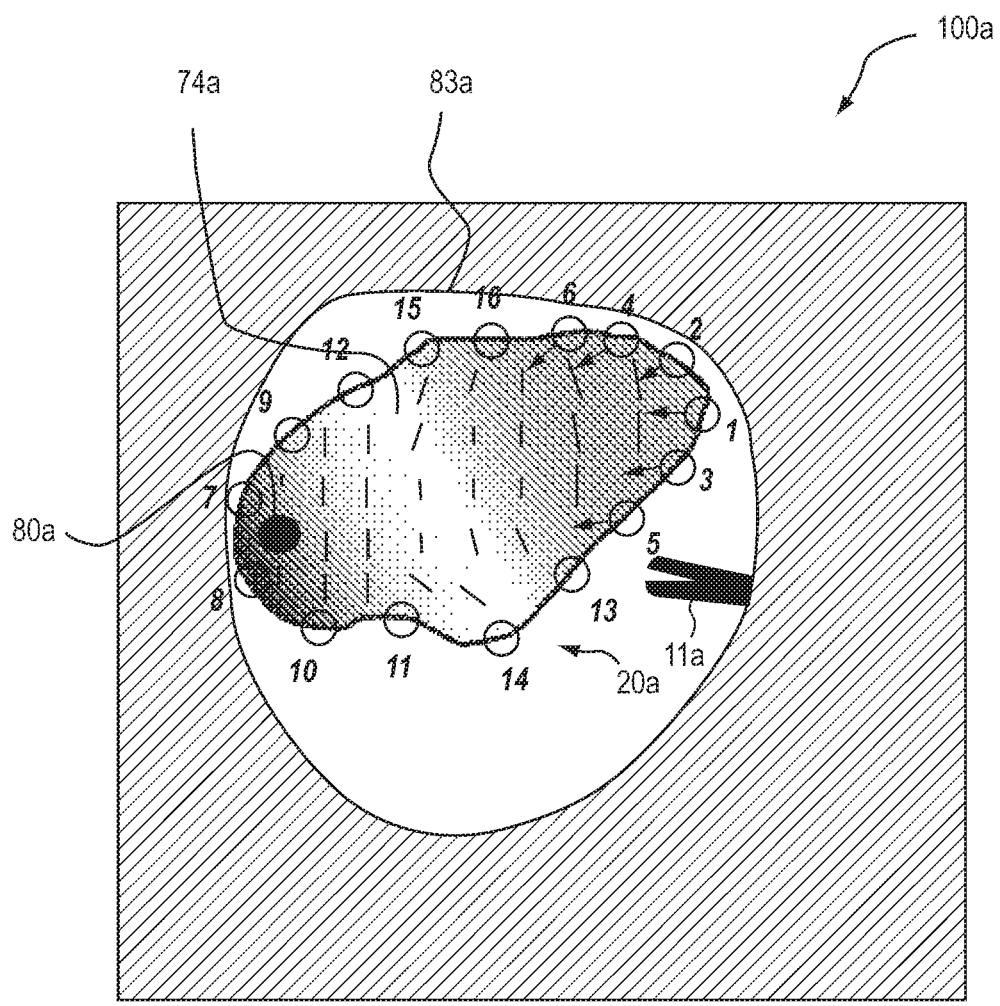
FIG. 7 is a schematic illustration of an output image which was generated with the aid of a colour and/or grey-scale value coding.

FIG. 7 shows an output image 100a which was generated by a system in accordance with an alternative exemplary embodiment. The illustration in FIG. 7 has elements that are analogous to illustrated elements in FIG. 6. These elements are therefore provided with similar reference signs, the latter having the accompanying symbol "a", however.

The output image 100a illustrated in FIG. 7 comprises a reproduction 20a of a region of the image plane image (shown in FIG. 3). The reproduction 20a was generated by means of a colour and/or grey-scale value coding. The reproduction 20a can therefore be for example a false colour representation of said region of the image plane image. The reproduction 20a is configured such that those regions in which a high lateral membrane stress occurs exhibit dark colouration. Therefore, the colour and/or grey-scale value coding of the reproduction 20a depends on the determined values of the stress-dependent parameters and furthermore on the measurement locations at which the values of the stress-dependent parameter were determined. In order to generate the reproduction, for each of a multiplicity of measurement locations, a region in the output image was determined which represents the respective measurement location. For each of the regions, a grey-scale and/or colour value was then determined depending on the values of the stress-dependent parameters which were determined at the corresponding measurement location.

The reproduction 20a is furthermore configured such that tissue structures of the corresponding region of the image plane image (shown in FIG. 3) are reproduced. By way of example, the reproduction 20a reproduces the fovea centralis 80. The retinal blood vessels 82 shown in FIG. 3 are likewise reproduced by the reproduction 20a, but are not illustrated in FIG. 7 for reasons of simplifying the illustration. The output image 100a, like the output image 100 illustrated in FIG. 6, was generated depending on a graphical representation. Said graphical representation is configured in a similar manner to the graphical representation 9 illustrated in FIG. 5. In particular, the output image 100a also shows local stress indicators which in each case indicate the direction of the highest lateral membrane stress. The output image 100a likewise reproduces a boundary marking, engagement point markings, and a numbering of the engagement point markings. However, it is also conceivable for the output image 100a to be generated without a graphical representation and merely to have the colour- and/or grey-scale-value-coded reproduction 20a.

The output images illustrated in FIGS. 6 and 7 yield a representation which allows a reliable and efficient examination or treatment of epiretinal gliosis.

The invention claimed is:

1. A System for examining an eye, comprising:
a microscopy system for generating an image plane image of an object region;
an OCT system, which is configured to acquire OCT data from the object region which reproduce the object region in different stress states; and
a data processing unit which is configured to determine at least one value of a stress-dependent parameter, depending on the OCT data;
wherein the system is configured to generate an output image, depending on the image plane image and furthermore depending on the stress-dependent parameter,
wherein the data processing unit is furthermore configured:
to determine a tissue structure image region, depending on the OCT data, wherein the tissue structure image region represents at least one part of a tissue structure; and
to determine the value of the stress-dependent parameter depending on the tissue structure image region determined.

2. The System according to claim 1, wherein the output image has a reproduction of at least one part of the image plane image;
wherein the data processing unit is configured to generate the reproduction by means of a colour and/or grey-scale value coding, and wherein the colour and/or grey-scale value coding is dependent on the value of the stress-dependent parameter.

3. The System according to claim 1, wherein the data processing unit is configured to generate a graphical representation depending on the value of the stress-dependent parameter; and
wherein the output image is generated by means of a superimposition of the graphical representation with at least one part of the image plane image.

4. The System according to claim 1, wherein the stress-dependent parameter is dependent on a stress in a membrane and/or a stress in an epiretinal membrane of the eye.

5. The System according to claim 1, wherein the stress-dependent parameter is dependent on a strain, a strain rate and/or an elasticity parameter in the object region.

6. The System according to claim 1,
wherein the data processing unit is configured to determine a location dependence of the stress-dependent parameter, depending on the OCT data; and
wherein the data processing unit is configured to generate the output image depending on the location dependence.

7. The System according to claim 1, wherein the data processing unit is determined to ascertain a parameter of a lateral extent of a tissue structure image region, depending on the OCT data;
wherein the tissue structure image region represents at least one part of a tissue structure;
wherein the lateral extent is measured parallel to an object plane of the microscopy system; and
wherein the data processing unit is configured to determine the output image depending on the parameter of the lateral extent.

8. The System according to claim 7, wherein the tissue structure image region represents a membrane, an epiretinal membrane and/or an inner limiting membrane.

9. The System according to claim 1, furthermore comprising an instrument configured for manipulating at least one part of the object region;
wherein the data processing unit is furthermore configured to determine a value of a supervisory parameter for supervision of the instrument depending on the OCT data; and
wherein the output image is furthermore dependent on the value of the supervisory parameter determined.

10. The System according to claim 9, wherein the data processing unit is configured to determine the supervisory parameter depending on the value of the stress-dependent parameter.

11. The System according to claim 1, wherein the object region comprises at least one part of a retina of the eye and/or at least one part of an epiretinal membrane.

12. A System for examining an eye comprising:
a data processing unit which is configured to read in OCT data which were acquired from an object region by means of an OCT system, wherein the object region comprises at least one part of an epiretinal membrane of the eye;
wherein the OCT data reproduce the object region for different stress states;
wherein the data processing unit is furthermore configured to determine a value of a stress-dependent parameter depending on the OCT data; and
wherein the stress-dependent parameter is dependent on a stress of the epiretinal membrane,
wherein the data processing unit is furthermore configured:
to determine a tissue structure image region, depending on the OCT data, wherein the tissue structure image region represents at least one part of an epiretinal membrane; and
to determine the value of the stress-dependent parameter depending on the tissue structure image region determined.

13. The System according to claim 12, wherein the data processing unit is furthermore configured to detect a location dependence of the stress-dependent parameter within the epiretinal membrane.

14. The System according to claim 12, wherein the stress of the epiretinal membrane is a lateral membrane stress of the epiretinal membrane.

15. A Method for operating a system, comprising:
generating an image plane image in an image plane of an object region by means of a microscopy system of the system;
acquiring OCT data from the object region by means of an OCT system of the system, wherein the OCT data reproduce the object region in different stress states;
determining a value of a stress-dependent parameter by means of a data processing unit of the system, depending on the OCT data; and
generating an output image, depending on the determined value of the stress-dependent parameter and depending on the image plane image,
wherein the data processing unit is furthermore configured:
to determine a tissue structure image region, depending on the OCT data, wherein the tissue structure image region represents at least one part of a tissue structure; and
to determine the value of the stress-dependent parameter depending on the tissue structure image region determined.

16. A Computer program product, comprising computer-readable instructions which, when loaded into the memory of a computer and/or computer network and executed by a computer and/or computer network, have the effect that the computer and/or the computer network perform(s) a method according to claim 15.

17. A Method for operating a system, comprising:
reading in OCT data by means of a data processing unit of the system; when the OCT data are acquired from an object region, wherein the object region comprises at least one part of an epiretinal membrane of an eye; and wherein the OCT data reproduce the object region for different stress states; and
determining a value of a stress-dependent parameter by means of the data processing unit, depending on the OCT data; wherein the stress-dependent parameter is dependent on a stress of the epiretinal membrane,
wherein the data processing unit is furthermore configured:
to determine a tissue structure image region, depending on the OCT data, wherein the tissue structure image region represents at least one part of an epiretinal membrane; and
to determine the value of the stress-dependent parameter depending on the tissue structure image region determined.

* * * * *

UNITED STATES PATENT AND TRADEMARK OFFICE
CERTIFICATE OF CORRECTION

| | | |
|---|---|---|
| PATENT NO. | : 9,629,537 B2 | |
| APPLICATION NO. | : 14/966728 | |
| DATED | : April 25, 2017 | |
| INVENTOR(S) | : Holger Matz et al. | |

It is certified that error appears in the above-identified patent and that said Letters Patent is hereby corrected as shown below:

In the Specification

Column 14, Line 60, "unit" should read --unit 5--

Column 16, Line 64, "representation" should read --representation.--

Signed and Sealed this
Eighth Day of August, 2017

Joseph Matal
*Performing the Functions and Duties of the*
*Under Secretary of Commerce for Intellectual Property and*
*Director of the United States Patent and Trademark Office*